(12) United States Patent
Barbachyn et al.

(10) Patent No.: US 6,605,609 B2
(45) Date of Patent: Aug. 12, 2003

(54) THIZAINE OXAZOLIDINONE

(75) Inventors: Michael Robert Barbachyn, Kalamazoo, MI (US); Gary Edward Zurenko, Kalamazoo, MI (US)

(73) Assignee: Pharmacia & Upjohn Company, Kalamazoo, MI (US)

(*) Notice: Subject to any disclaimer, the term of this patent is extended or adjusted under 35 U.S.C. 154(b) by 0 days.

(21) Appl. No.: 09/881,189

(22) Filed: Jun. 15, 2001

(65) Prior Publication Data

US 2002/0156072 A1 Oct. 24, 2002

Related U.S. Application Data

(60) Provisional application No. 60/212,474, filed on Jun. 16, 2000, provisional application No. 60/236,595, filed on Sep. 29, 2000, and provisional application No. 60/285,587, filed on Apr. 20, 2001.

(51) Int. Cl.[7] ................... A61K 31/541; C07D 417/10
(52) U.S. Cl. ................ 514/227.8; 544/58.2; 544/58.7; 544/60
(58) Field of Search ................. 544/58.2; 514/227.8

(56) References Cited

U.S. PATENT DOCUMENTS

| | | | |
|---|---|---|---|
| 5,688,792 A | * 11/1997 | Barbachyn et al. | 514/235.5 |
| 5,880,118 A | 3/1999 | Barbachyn et al. | 514/211 |
| 5,968,962 A | 10/1999 | Thomas et al. | 514/376 |
| 5,981,528 A | 11/1999 | Gravestock | 514/252 |

FOREIGN PATENT DOCUMENTS

| | | |
|---|---|---|
| WO | WO 98/40056 | 9/1998 |
| WO | WO 01/34128 | 5/2001 |

OTHER PUBLICATIONS

Derwent Publication Lts., London, GB; AN 1971–77687S; XP002195988 & SU 288 214 A [Uralsk BR Chemical Product].

* cited by examiner

*Primary Examiner*—Richard L. Raymond
(74) *Attorney, Agent, or Firm*—Lucy X. Yang; Jonathan P. O'Brien

(57) ABSTRACT

The present invention provides a thizaine oxazolidinone useful as antimicrobial.

51 Claims, No Drawings

THIZAINE OXAZOLIDINONE

CROSS REFERENCE TO RELATED APPLICATIONS

This application claims the benefit of the following provisional applications: U.S. Ser. No. 60/212,474, filed Jun. 16, 2000; U.S. Ser. No. 60/236,595, filed Sep. 29, 2000; and U.S. Ser. No. 60/285,587, filed Apr. 20, 2001, under 35 USC 119(e)(i).

FILED OF THE INVENTION

The present invention describes a novel compound, N-({(5S)-3-[4-(1,1-dioxido-4-thiomorpholinyl)-3,5-difluorophenyl]-2-oxo-1,3-oxazolidin-5-yl}methyl) acetamide, a new antimicrobial combination therapy for infective diseases caused by gram-positive and gram-negative bacteria, and compositions particularly useful for oral and intravenous administration.

BACKGROUND OF THE INVENTION

The oxazolidinone antibacterial agents are a novel synthetic class of antimicrobials with broad activity against a number of human and veterinary pathogens, including gram-positive aerobic bacteria such as multiply-resistant staphylococci and streptococci, gram-negative aerobic bacteria such as *H. influenzae* and *M. catarrhalis*, as well as anaerobic organisms such as bacteroides and clostridia species, and acid-fast organisms such as *Mycobacterium tuberculosis* and *Mycobacterium avium*. It is also known that as a chemical compound class, oxazolidinones generally inhibit to some extent monoamine oxidase (MAO), the enzyme responsible for preventing acute blood pressure elevation by the endogenous and dietary amine, tyramine, and other sympathomimetic amines. Accordingly, there is a demand to discover oxazolidinone antibiotics that possess minimum MAO inhibitory activity to eliminate the related side effects from potential drug-drug interactions.

The present invention provides N-({(5S)-3-[4-(1,1-dioxido-4-thiomorpholinyl)-3,5-difluorophenyl]-2-oxo-1,3-oxazolidin-5-yl}methyl)acetamide. This compound has potent activity against gram-positive human and veterinary pathogens. In particular, it has unexpectedly weak MAO inhibitory activity, which indicates that this compound possesses the capacity to minimize or eliminate potential drug-drug interactions since strong inhibition of monoamine oxidase can result in altered clearance rates for other compounds normally metabolized by it.

In addition, many gram-positive organisms have developed significant levels of resistance to other antibiotics. However, N-({(5S)-3-[4-(1,1-dioxido-4-thiomorpholinyl)-3,5-difluorophenyl]-2-oxo-1,3-oxazolidin-5-yl}methyl) acetamide exhibits potent activity against gram-positive pathogens that are resistant to other gram-positive antibiotics. Therefore, it is beneficiary in a medical treatment to combine the compound of the present invention with other gram-positive antibiotics to achieve broad coverage and synergistic interactions. The present invention provides a method for treating gram-positive infection in a mammal by using the compound of the present invention, either individually, or in combination with other gram-positive antibiotics.

Furthermore, in medical treatments, a physician often does not know for sure whether the infections are caused by gram-positive bacteria, or gram-negative bacteria or both. Therefore, a need remains for combination therapy to assure coverage of all pathogens in a potentially mixed infection. The present invention provides a combination therapy by using the compound of the present invention in combination with other gram-negative antibiotics.

The present invention further provides compositions suitable for oral and intravenous administrations.

U.S. Pat. No. 5,880,118 discloses substituted oxazine and thiazine oxazolidinone antimicrobials. U.S. Pat. No. 6,968,962 discloses phenyloxazolidinones having a C—C bond to 4–8 membered heterocyclic rings. U.S. Pat. No. 5,981,528 discloses antibiotic oxazolidinone derivatives. PCT patent application, Ser. No. PCT/US00/28872 disclose admixture of linezolid and other antibacterial agents.

None of the references cited above specifically contemplates the compound of the present invention, its combination therapy and its novel compositions.

SUMMARY OF THE INVENTION

The present invention provides a novel oxazolidinone compound of formula I

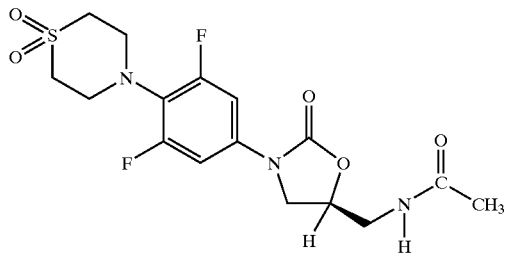

or its pharmaceutically acceptable salt.

The present invention further provides a method for treating gram-positive bacterial infections which comprises administration to a mammal being treated a pharmaceutically effective amount of the compound of formula I, either individually, or in combination with other gram-positive antibiotics.

The present invention further provides a method for treating gram-positive and gram-negative bacterial infections which comprises administration to a mammal being treated a pharmaceutically effective amount of the compound of formula I in combination with at least one other gram-negative antibiotic.

The present invention further provides compositions for treating gram-positive bacterial infections wherein the compositions comprise a pharmaceutically effective amount of the compound of formula I and at least one other gram-positive antibiotic.

The present invention further provides compositions for treating gram-positive and gram-negative bacterial infections wherein the compositions comprise a pharmaceutically effective amount of the compound of formula I and at least one other gram-negative antibiotic.

The present invention further provides an aqueous composition suitable for intravenous administration for the treatment of gram-positive and/or gram-negative bacterial infections wherein the composition comprises a pharmaceutically effective amount of the compound of formula I and at least one other gram-negative antibiotic.

The present invention further provides a composition suitable for oral administration for the treatment of gram-positive and/or gram-negative bacterial infections wherein the composition comprises a pharmaceutically effective amount of the compound of formula I and at least one other gram-negative antibiotic.

The present invention further provides a use of the compound of formula I to prepare a medicament, for treating gram-positive and/or gram-negative bacterial infections.

DETAILED DESCRIPTION OF THE INVENTION

Definitions

The term "antibiotic" refers to an antibacterial agent other than the compound of the present invention.

Specifically, they refer to Amikacin, Gentamicin, Spectinomycin, Tobramycin, Imipenem, Meropenem, Cefadroxil, Cefazolin, Cephalexin, Cefaclor, Cefotetan, Cefoxitin, Cefprozil, Cefuroxime, Loracarbef, Cefdinir, Cefixime, Cefoperazone, Cefotaxime, Cefpodoxime, Ceftazidime, Ceftibuten, Ceftozoxime, Ceftriaxone, Cefepime, Azithromycin, Clarithromycin, Dirithromycin, Penicillin G, Cloxacillin, Dicloxacillin, Nafcillin, Oxacillin, Amoxicillin, Amoxicillin, Ampicillin, Mezlocillin, Piperacillin, Nalidixic Acid, Ciprofloxacin, Enoxacin, Lomefloxacin, Norfloxacin, Ofloxacin, Levofloxacin, Sparfloxacin, Alatrofloxacin, Gatifloxacin, Moxifloxacin, Trimethoprim, Sulfisoxazole, Sulfamethoxazole, Doxycycline, Minocycline, Tetracycline, Aztreonam, Chloramphenicol, Clindamycin, Quinupristin, Fosfomycin, Metronidazole, Nitrofurantoin, Rifampin, Trimethoprim, and Vancomycin. All of them are known. They can be either obtained commercially or be prepared according to the references cited in PHYSICIANS' DESK REFERENCE, the 53$^{rd}$ Edition (1999) and the US FDA's Orange book.

The term "gram-positive antibiotic" refers to an antibacterial agent active against gram-positive bacterial organisms.

The term "gram-negative antibiotic" refers to an antibacterial agent active against gram-negative bacterial organisms.

Methods for Preparation

The compound of the present invention, N-({(5S)-3-[4-(1,1-dioxido-4-thiomorpholinyl)-3,5-difluorophenyl]-2-oxo-1,3-oxazolidin-5-yl}methyl)acetamide, can be prepared according to the procedures described herein below.

Method 1

Step 1 Preparation of 4-(2,6-difluoro-4-nitrophenyl) thiomorpholine 2,6-Difluoro-4-nitrophenyl trifluoromethanesulfonate (992 mg, 3.23 mmol) is dissolved in dry tetrahydrofuran (15 mL) and then treated dropwise with thiomorpholine (0.487 mL, 4.85 mmol). The reaction is then heated to reflux (70° C.) under nitrogen for 16 hours. The reaction is then allowed to cool to room temperature, stirring over the weekend (56 hours) under nitrogen. At this time, the reaction is found to be complete by thin layer chromatography. The reaction mixture is concentrated under reduced pressure to yield a yellow solid and then absorbed onto silica gel (25 g). The material is then chromatographed on more silica gel (75 g, packed with hexane), eluting with 5% ethyl acetate/hexane to give 535 mg (64%) of the title compound as a solid, mp: 104–105° C.

MS (EI) m/z (rel. intensity) 260 (M$^+$, 81), 260 (81), 245 (24), 213 (31), 186 (99), 156 (18), 140 (18), 139 (14), 74 (15), 56 (26), 46 (32).

Step 2 Preparation of benzyl 3,5-difluoro-4-(4-thiomorpholinyl)phenyl carbamate 4-(2,6-Difluoro-4-nitrophenyl)thiomorpholine (27.5 g, 0.106 mol) is dissolved in 80 mL of tertrahydrofuran and then transferred to a Parr vessel containing 6.0 g of Raney Nickel catalyst in a water slurry. 180 mL of 30% water/tetrahydrofuran is also added to the Parr vessel. The reaction mixture is then hydrogenated at 40 psi on the Parr Shaker overnight. More hydrogen has to be added several times during the course of the reaction. The following morning the reaction is complete as indicated by thin layer chromatography. The catalyst is filtered off through Celite, washing the filter cake with tetrahydrofuran. Another 50 mL of water is added and the tetrahydrofuran/water solution is cooled to 0° C. with an ice bath. After the addition of solid sodium bicarbonate (35.5 g, 0.423 mol) and benzyl chloroformate (27.04 g, 22.6 mL, 0.158 mol), the ice bath is removed and the reaction mixture stirred under nitrogen over the weekend. The reaction mixture is then diluted with ethyl acetate and water, transferred to a separatory funnel, and extracted with ethyl acetate. The phases are separated and the organic extracts are washed with water and brine, then dried with sodium sulfate, filtered, and concentrated to yield a dark orange-brown solid. The crude material is dissolved in methylene chloride and chromatographed on silica gel, eluting with methylene chloride. Appropriate fractions are combined and concentrated to yield 24.23 g (63%) of the title compound as a solid, mp: 132.5–134.5° C.

MS (ESI+) for m/z 365 (M+H)$^{30}$, MS (ESI−) for m/z 363 (M−H)$^−$.

Step 3 Preparation of N-({(5S)-3-[3,5-difluoro-4-(4-thiomorpholinyl)phenyl]-2-oxo-1,3-oxazolidin-5-yl}methyl)acetamide Benzyl 3,5-difluoro-4-(4-thiomorpholinyl)phenyl carbamate (4.27 g, 11.71 mmol) along with (S)-N-[2-(acetyloxy)-3-chloropropyl]acetamide (2 eq, 4.54 g, 23.42 mmol) is dissolved in anhydrous N,N-dimethylformamide. The resultant solution is treated with anhydrous methanol (2 eq, 0.75 g, 0.95 mL, 23.42 mmol), followed by the addition of lithium tert-butoxide (1.0 M solution in hexanes, 35.13 mL, 35.13 mmol) via syringe pump over two hours. The biphasic reaction mixture then stirred overnight under nitrogen at room temperature. The following day, the reaction is quenched with acetic acid (2 eq, 1.41 g, 1.34 mL, 23.42 mmol) and then 13 mL of methanol are added to extract the product out of the hexane layer. The phases are separated, and the hexane layer is washed three times with a 4:1 methanol: water solution. The methanol extracts are combined with the original N,N-dimethylformamide layer and the combined layers are extracted with methylene chloride and water. The methylene chloride layer is then dried with sodium sulfate, filtered, and concentrated. The crude product is chromatographed on silica gel, eluting with methylene chloride and solutions of 2% and 5% methanol/methylene chloride to yield 3.43 g of the title compound as an off-white solid (79%), mp: 187–188.5° C.

MS (ESI+) for m/z 372 (M+H)$^+$, MS (ESI−) for m/z 394 (M+Na)$^+$, MS (ESI) for m/z 370 (M−H)$^−$.

Step 4 Preparation of N-({(5S)-3-[4-(1,1-dioxido-4-thiomorpholinyl)-3,5-difluorophenyl]-2-oxo-1,3-oxazolidin-5-yl}methyl)acetamide N-({(5S)-3-[3,5-difluoro-4-(4-thiomorpholinyl)phenyl]-2-oxo-1,3-oxazolidin-5-yl}methyl)acetamide (13.36 g, 35.97 mmol) is dissolved in a solution of 25% water/acetone and then treated sequentially with 4-Methylmorpholine N-oxide (3 eq, 12.64 g, 107.91 mmol) and a catalytic amount of osmium tetroxide (2.8 mL). The reaction is stirred overnight at room temperature under nitrogen. In the morning, another 2 mL of osmium tetroxide is added. Another 2 eq of 4-Methylmorpholine N-oxide and 2.5 mL of osmium tetroxide are added a few hours later. The reaction is stirred overnight again under nitrogen. The following morning, the reaction is complete. The reaction mixture is quenched with a solution of sodium hydrosulfite and then extracted with methylene chloride three times. The organic layer is washed with sodium hydrosulfite and brine, dried with sodium sulfate, filtered, and concentrated. The crude product is then chomatographed on silica gel, eluting with methylene chloride and then 2% and 5% methanol/methylene chloride solutions. Appropriate fractions are combined and concentrated to yield 11.99 g (83%) of the title compound as a white solid, mp: 187–189.5° C.

MS (ESI+) for m/z 404 (M+H)$^+$, MS (ESI+) for m/z 426 (M+Na)$^+$, MS (ESI–) for m/z 402 (M–H)$^-$.

Method 2

Step 1 Preparation of 4-(2,6-difluorophenyl)thiomorpholine 1,1-dioxide

Aluminum chloride (310 g, 2.3 mol) is added to chlorobenzene (2.5 L) to give a cloudy green suspension. Vinyl sulfone (230 mL, 2.3 mol) is added via a funnel. 2,6-Difluoroaniline (250 mL, 2.3 mol) is added a via funnel. The light brown solution is heated to 110° C. Upon completion, the heat is removed and the black solution is self-cooled to 70° C. The reaction mixture is quenched in methylene chloride (4 L) and ice water (5 L). The aqueous phase is extracted with methylene chloride. The combined organic layers are concentrated and added branched octane (3 L), and then cooled to 0° C. for 30 minutes. The solids are filtered and washed with branched octane (2×500 mL). The crude black solids are dissolved into methylene chloride (3 L) and then loaded onto a SiO$_2$ plug (1.8 kg). The column is eluted with dichloromethane (16 L) until clear. The methylene chloride solution is concentrated to give light brown solids (387 g or 68% yield). The solids are dissolved in hot ethyl acetate (3 L) followed by the addition of hexanes (900 mL). The black solution is self-cooled to room temperature overnight. The light amber crystal needles are filtered and washed with hexanes (4×250 mL). The solids are dried in vacuo at 50° C. overnight to give 314 g of the title compound (55% recystallized yield 1$^{st}$ crop).

$^1$H NMR (CDCl$_3$) (δ): 7.08 (m, 1H), 6.91 (m, 2H), 3.67 (m, 4H), 3.18 (m, 4H).

Step 2 Preparation of 4-(2,6-difluoro-4-nitrophenyl)thiomorpholine 1,1-dioxide

To a suspension of the product of example 1 (300 g, 1.21 mol) in 3 L of acetic acid, nitric acid (255 mL, ca. 6 mol, fuming, 90%) is added over 30 min at room temperature. Yellow precipitate is formed within minutes and increases over time. The reaction is kept at room temperature for 18 hours, before it is poured into 6 L of water. After stirred for 2 hours, the yellow suspension is filtered. The precipitate is washed with water (1.5 L×3) and EtOH (0.5 L×2) and dried in oven at 50° C. overnight to give 333 g (94%) of the title compound as a solid.

$^1$H NMR (DMSO-d$_6$) (δ): 8.05 (m, 2H), 3.69 (m, 4H), 3.26 (m, 4H).

Step 3 Preparation of 4-(1,1-dioxido-4-thiomorpholinyl)-3,5-difluoroaniline

To an autoclave is added the product of example 2 (7.0 kg, 24 moles, 1.0 eq). Raney Nickel (1.4 kg) is activated and suspended in 4 L of THF. The slurry is added to the autoclave followed by additional THF (66 L). The mixture is heated at 40° C. and under 40 psi H$_2$ till completion. The mixture is filtered and the filtrate is directly used in the next step. A small portion of the filtrate is concentrated and recrystallized in isopropanol to give the title compound.

$^1$H NMR (DMSO-d$_6$) (δ): 6.17 (m, 2H), 5.35 (s, 2H), 3.32 (m, 4H), 3.15 (m, 4H).

Step 4 Preparation of isobutyl 4-(1,1-dioxido-4-thiomorpholinyl)-3,5-difluorophenylcarbamate To the 400 L glass-lined reactor containing the product of example 3 in THF (12.6 kg, 48 moles, 1.0 eq) solutions is added 47% potassium carbonate solution (14.1 kg, 48 moles, 1.0 eq). The mixture is heated to ca 45° C. Isobutyl chloroformate (7.2 kg, 53 moles, 1.1 eq) is added to the mixture while maintaining a reaction temperature between 45° C. and 55° C. The reaction is stirred at 45° C and 55° C. Once deemed complete, the reaction is quenched by slowly adding water (45 L) over 15 minutes. The reaction mixture is cooled to 25° C. and the phases separated. The THF solution is swapped to a 150 L of isopropanol and 50 L of water suspension. The slurry is slowly cooled to 5° C. Then, the yellow slurry is filtered and the cake washed with cold isopropanol (2×30 L). The yellow solids are dried with 60° C. N$_2$ to give the title compound as a solid (14.2 kg, 82% yield).

$^1$H NMR (CDCl$_3$) (δ): 7.02 (m, 2H), 6.81 (s, 1H), 3.95 (d, 2H), 3.60 (m, 4H) 3.17 (m, 4H), 1.97 (m, 1H), 0.94 (d, 6H)

Step 5 Preparation of N-({(5S)-3-[4-(1,1-dioxido-4-thiomorpholinyl)-3,5-difluorophenyl]-2-oxo-1,3-oxazolidin-5-yl}methyl)acetamide To a dry, nitrogen purged 400 L glass-lined reactor is added LiOtBu (6.96 kg, 87 moles, 3.0 eq), the product of example 4 (10.50 kg, 29 moles, 1.0 eq), and branched octane (70 L). The slurry is cooled to ca 20° C. Then, DMF (10 L) is slowly added over 25 min and the slurry is stirred for 30 min. Methanol (1.86 kg, 58 moles, 2.0 eq) is slowly added over 25 min. The line is rinsed with branched octane (1 L) and the slurry stirred at ca 15° C. To a dry, nitrogen purged 200 L glass-lined reactor is added (S)-N-[2-(acetyloxy)-3-chloropropyl]acetamide (11.22 kg, 58 moles, 2.0 eq) and DMF (9.4 L). (S)-N-[2-(acetyloxy)-3-chloropropyl]acetamide is known in the art and can be prepared according to the procedures described in Tetrahedron Letters, Vol. 37, No. 44, pp. 7937–7940 and WO 9924393. The solution is stirred at ca 25° C. to 30° C. for 1 hours for complete solid dissolution. This light yellow solution is slowly added to the slurry over 1.5 hours while maintaining the temperature between 15° C. and 16° C. The line is rinsed with branched octane (20 L). At 15 h, HPLC assay indicated ca 94% conversion. Glacial acetic acid (3.48 kg, 58 moles, 2.0 eq) is slowly added over 30 min followed by a line rinse of methanol (14 L). The biphasic solution is stirred for 1 hour and then separated. The upper organic phase is re-extracted with methanol (14 L) and DW water (4.7 L). The layers are separated. To the combined lower aqueous organic phase is added CH$_2$Cl$_2$ (32 L) and DW water (32 L). The biphasic solution is stirred and the layers separated. The aqueous phase is re-extracted twice with CH$_2$Cl$_2$ (2×11 L). The combined organic layers are then distilled under vacuum to ca 70 L and n-BuOH (210 L) is then slowly added while maintaining distillation and a total volume of ca 80 L. Once the addition is complete, the slurry is concentrated to a final volume of ca 58 L and cooled to ca 40° C. Isopropyl alcohol (53 L) is slowly added to the slurry over 30 min and then slowly cooled further to 0° C. over 2 hours. After stirring for 30 min, the solids are filtered and the cake is washed three times with cold isopropanol (3×53 L). The yellow solids are dried with 60° C. N$_2$ to give the title compound as a solid (9.3 kg, 79% yield).

1H NMR (DMSO-δ$_6$) 1.83 (s, 3H), 3.20–3.24 (m, 4H), 3.40 (t, J=5.6 Hz, 2H), 3.47–3.51 (m, 4H), 3.70 (dd, J=9.0 Hz, J=7.9 Hz, 1H), 4.09 (t, J=9.0 Hz, 1H), 4.6–4.78 (m, 1H), 7.29 (s, 1H), 7.32 (s, 1H), 8.21 (t, J=5.6 Hz, 1H).

Activity Data

The in vitro activity of the compound of this invention can be assessed by standard testing procedures such as the determination of minimum inhibitory concentration (MIC) by agar dilution as described in "Approved Standard. Methods for Dilution Antimicrobial Susceptibility Tests for Bacteria That Grow Aerobically", 3rd. ed., published 1993 by the National Committee for Clinical Laboratory Standards, Villanova, Pa., USA. The activity of compounds of this invention against *Staphylococcus aureus* is shown in Table 1.

Oxazolidinones with weak or no ability to inhibit MAO-A have the potential to minimize or eliminate potential drug-drug interactions. The compound of the present invention was tested for their MAO inhibitory activity by using the procedures below.

The enzyme assay for human MAO-A relies on the formation of a colored reaction product by the enzyme. This product is detected by a spectrophotometer at 421 nm. The chromogenic substrate was 1-methyl-4-(1-methyl-2-pyrryl)-1,2,3,6-tetrahydropyridine. Membrane bound, human placental MAO-A was solubilized and purified as described and used as a concentrated solution (5 nmoles per ml). See: Flaherty P, Castagnoli K, Wang Y-X, Castagnoli Jr. N., *J Med Chem*. Vol. 39, p. 4756, (1996).

Stock Solutions—Sodium phosphate was prepared as a 50 mM stock solution, pH 7.3 at 37° C. Stock solutions (50 mM) of the test compounds were prepared in DMSO. Serial dilutions of the 50 mM stocks were made in DMSO to form additional stock solutions ranging from 20 mM to 0.3125 mM. These stocks were then frozen until needed. The stocks were diluted 1/100 into the final enzyme assay volume at the time of assay. A 10 mM stock solution of the chromogenic substrate was prepared in the 50 mM phosphate buffer, aliquoted and then frozen until time of use.

Enzyme Assay—Initial velocity assays were run in a SPECTRAmax 250 microplate spectrophotometer (Molecular Devices Corp., Sunnyvale, Calif.). The final composition of the assay solution was 0.05 M sodium phosphate, pH 7.3, 80 mM substrate, inhibitor concentrations ranging up to 500 mM, 1% DMSO, and sufficient enzyme to produce an absorbency change at 421 nm of 0.0015–0.002 min. The reactions were run at 37° C. The reaction was followed by recording the increase in absorbency at 421 nm. Inhibitors were pre-incubated with the MAO-A in the reaction mixture for 15 min. prior to starting the reaction. Ki values were determined from the initial velocity data using the following equation. See Segel, I. H., *Enzyme Kinetics*. Vol. 957, p. 105, (1975). Wiley Interscience. New York, N.Y. $\%\text{Inh.}=100*[I]/([I]+Ki(1+[S]/Km_{(S)})$. The results are also shown in Table 1.

TABLE 1

(Comparison of the compound of formula 1 with linezolid)

| Compound | $MIC_{90}$[1]<br>S. aureus (52 isolates),<br>methicillin-resistant<br>($\mu$g/mL) | MAO-A Ki[2]<br>($\mu$M) |
|---|---|---|
| The compound of formula I | 2 | 101 |
| linezolid | 4 | 53 |

[1]$MIC_{90}$ = minimum inhibitory concentration required to inhibit 90% of the isolates (lower number is better). [2]Ki for human monoamine oxidase A (higher number is better).

Pharmaceutical Salts

The compound of formula I may be used in its native form or as a salt. In cases where forming a stable nontoxic acid or base salt is desired, administration of the compound as a pharmaceutically acceptable salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, etoglutarate, and glycerophosphate. Suitable inorganic salts may also be formed, including hydrochloride, hydrobromide, sulfate, nitrate, bicarbonate, and carbonate salts.

Pharmaceutically acceptable salts may be obtained using standard procedures well known in the art, for example, reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Doses for Individual/Combination Therapy

In combating the infective diseases caused by gram-positive organisms, the compound of the formula I can be used either individually, or in combination with other antibiotics that are active against gram-positive organisms. Some of the gram-positive antibiotics may also have activity against gram-negative organisms.

Examples of such gram-positive antibiotics are listed in Table 2.

TABLE 2

Gram-Positive Antibiotics That May Be Used
In a Combination Therapy With The Compound of Formula I

| AGENTS | LO DOSE | HI DOSE | STD DOSE |
|---|---|---|---|
| AMINOGLYCOSIDES | | | |
| Amikacin | | | 15 mg/kg/day |
| Gentamicin | 1 mg/kg/day<br>.5 mg/kg | 5 mg/kg/day<br>2.5 mg/kg | |
| Spectinomycin | | | 40 mg/kg |
| Tobramycin | 1 mg/kg/day<br>.5 mg/kg/day | 5 mg/kg/day<br>5 mg/kg/day | |
| PENEMS | | | |
| Imipenem/cilastatin | 62.5 mg<br>6.25 mg/kg | 1 g<br>25 mg/kg | |
| Meropenem | .5 mg/kg | 2.5 mg/kg | 40 mg/kg |
| 1ST GEN CEPHS | | | |
| Cefadroxil | .25 g/day | 2 g/day | 30 mg/kg/day |

TABLE 2-continued

Gram-Positive Antibiotics That May Be Used
In a Combination Therapy With The Compound of Formula I

| AGENTS | LO DOSE | HI DOSE | STD DOSE |
|---|---|---|---|
| Cefazolin | 62.5 mg | 1.5 g | |
| | 6.25 mg/kg/day | 100 mg/kg/day | |
| Cephalexin | 62.5 mg | 500 mg | |
| | 6.25 mg/kg/day | 50 mg/kg/day | |
| 2$^{ND}$ GEN CEPHS | | | |
| Cefaclor | 62.5 mg | 500 mg | |
| | 5 mg/kg/day | 40 mg/kg/day | |
| Cefotetan | 0.125 g | 3 g | |
| | 10 mg/kg/day | 80 mg/kg/day | |
| Cefoxitin | .25 g | 3 g | |
| | 20 mg/kg/day | 160 mg/kg/day | |
| Cefprozil | 62.5 mg | 500 mg | |
| | 1.87 mg/kg/dose | 15 mg/kg/dose | |
| Cefuroxime | 187.5 mg | 3 g | |
| | 31.25 mg | 500 mg | |
| | 12.5 mg/kg/day | 150 mg/kg/day | |
| | 31.25 mg/kg/day | 500 mg/kg/day | |
| Loracarbef | 50 mg | 400 mg | |
| | 3.75 mg/kg/day | 500 mg/kg/day | |
| 3$^{RD}$ GEN CEPHS | | | |
| Cefdinir | 75 mg | | 600 mg |
| Cefixime | 50 mg | | 400 mg |
| Cefoperazone | .5 g/day | 12 g/day | |
| | 25 mg/kg/day | 150 mg/kg/day | |
| Cefotaxime | .25 g | 2 g | |
| | 12.5 mg/kg/dose | 300 mg/kg/day | |
| Cefpodoxime | 25 mg | 400 mg | 10 mg/kg/day |
| Ceftazidime | 62.5 mg | 2 g q8 | |
| | 25 mg/kg/day | 150 mg/kg/day | |
| Ceftibuten | 2.25 mg/kg | 400 mg | 400 mg |
| Ceftozoxime | .25 g | 4 g | |
| | 12.5 mg/kg/day | 200 mg/kg/day | |
| Ceftriaxone | 31.25 mg | 2 g | |
| | 12.5 mg/kg/day | 100 mg/kg/day | |
| 4$^{TH}$ GEN CEPHS | | | |
| Cefepime | 0.125 g | 2 g | |
| | 12.5 mg/kg | 50 mg/kg q8 | |
| MACROLIDES | | | |
| Azithromycin | 62.5 mg | 500 mg | |
| | 62.5 mg | 500 mg | |
| Clarithromycin | 62.5 mg | 500 mg | 7.5 mg/kg/day |
| Dirithromycin | | | 500 mg |
| 1$^{ST}$ GEN PENS | | | |
| Penicillin G | 2 million units/day | 30 million units/day | |
| | 2000 units/kg/dy | 400,000 units/kg/day | |
| 2$^{ND}$ GEN PENS | | | |
| Cloxacillin | 62.5 mg | 500 mg | |
| | 12.5 mg/kg/day | 100 mg/kg/day | |
| Dicloxacillin | 31.25 mg | 500 mg | |
| | 3.125 mg/kg/day | 100 mg/kg/day | |
| Nafcillin | 125 mg | 2 g | |
| | 2.5 mg/kg | 25 mg/kg | |
| Oxacillin | 62.5 mg | 2 g | |
| | 125 mg | 1000 mg | |
| | 25 mg/kg/day | 200 mg/kg/day | |
| | 12.5 mg/kg/day | 100 mg/kg/day | |
| 3$^{RD}$ GEN PENS | | | |
| Amoxicillin | 62.5 mg | 875 mg | |
| | 5 mg/kg/day | 45 mg/kg | |
| Amoxicillin/clavulanic acid | 62.5 mg | 875 mg | |
| | 6.25 mg/kg/day | 45 mg/kg/day | |

TABLE 2-continued

Gram-Positive Antibiotics That May Be Used
In a Combination Therapy With The Compound of Formula I

| AGENTS | LO DOSE | HI DOSE | STD DOSE |
|---|---|---|---|
| Ampicillin | 62.5 mg | 12 g/day q4 | |
| | 6.25 mg/kg/day | 300 mg/kg/day | |
| Ampicillin/sulbactam | 0.375 g | 3 g | 300 mg/kg/day |
| 4$^{TH}$ GEN PENS | | | |
| Mezlocillin | 0.375 g | 4 g | 75 mg/kg |
| Piperacillin | 1.5 g/day | 24 g day | |
| | 25 mg/kg/day | 300 mg/kg/day | |
| Piperacillin/tazobactam | | | 240 mg/kg/day |
| Ticarcillin | .25 g | 4 g | |
| | 12.5 mg/kg/day | 300 mg/kg/day | |
| Ticarcillin/clavulanate | 50 mg/kg/day | 300 mg/kg/day | |
| | 0.775 g | 3.1 g | |
| 1$^{ST}$ GEN QUINOLONES | | | |
| Nalidixic Acid | | | 55 mg/kg/day |
| 2$^{ND}$ GEN QUINOLONES | | | |
| Ciprofloxacin | 50 mg | 750 mg | |
| | 2.5 mg/kg/dose | 15 mg/kg/dose | |
| | 62.5 mg | 750 mg | |
| | 2.5 mg/kg/dose | 15 mg/kg/dose | |
| Enoxacin | 50 mg | 400 mg | |
| Lomefloxacin | | | 400 mg |
| Norfloxacin | | | 400 mg |
| Ofloxacin | 50 mg | 400 mg | |
| 3$^{RD}$ GEN QUINOLONES | | | |
| Levofloxacin | 62.5 mg | 750 mg | |
| Sparfloxacin | 50 mg | 400 mg | |
| 4$^{TH}$ GEN QUINOLONES | | | |
| Alatrofloxacin | 50 mg | 300 mg | |
| Gatifloxacin | 50 mg | 400 mg | |
| Moxifloxacin | | | 400 mg |
| SULFAS | | | |
| Trimethoprim/sulfamethoxazole | 15 mg | 800 mg | |
| | 3.75 mg/day | 150 mg/day | |
| Sulfisoxazole | 18.75 mg | 150 mg | |
| Sulfamethoxazole | .25 g | 2 g | |
| TETRACYCLINES | | | |
| Doxycycline | 5 mg | 100 mg | |
| Minocycline | 25 mg | 200 mg | |
| Tetracycline | 62.5 mg | 500 mg | |
| OTHER | | | |
| Chloramphenicol | 12.5 mg/kg/day | 100 mg/kg/day | |
| Clindamycin | 150 mg | 900 mg | |
| | 37.5 mg | 450 mg | |
| | 5 mg/kg/day | 40 mg/kg/day | |
| | 2 mg/kg/day | 25 mg/kg/day | |
| Quinupristin/dalfopristin | 1.875 mg/kg | 7.5 mg/kg q8 | |
| Fosfomycin | | | 3 g |
| Nitrofurantoin | 12.5 mg | 100 mg | |
| | 1.25 mg/kg/day | 7 mg/kg/day | |
| Rifampin | 2.5 mg/kg | 600 mg/kg | |
| | 2.5 mg/kg | 600 mg/kg | |
| Trimethoprim | 25 mg | 200 mg | 10 mg/kg/day |
| Vancomycin | | | 1 g |
| | 2.5 mg/kg q6 | 15 mg/kg q8 | |

In combating the infective diseases caused by gram-positive and gram-positive organisms, the compound of the formula I can be used in combination with other antibiotics that are active against gram-negative organisms. Examples of such gram-negative antibiotics are listed in Table 3. Some of gram-negative antibiotics may also have activity against gram-positive organisms.

TABLE 3

Gram-Negative Antibiotics That May Be Used
In a Combination Therapy with The Compound of Formula I

| AGENTS | LO DOSE | HI DOSE | STD DOSE |
|---|---|---|---|
| AMINOGLYCOSIDES | | | |
| Amikacin | | | 15 mg/kg/day |
| Gentamicin | 0.75 mg/kg/day | 5 mg/kg/day | |
|  | 0.5 mg/kg | 2.5 mg/kg | |
| Spectinomycin | | | 40 mg/kg |
| Tobramycin | 0.75 mg/kg/day | 5 mg/kg/day | |
|  | 0.5 mg/kg/day | 5 mg/kg/day | |
| PENEMS | | | |
| Imipenem/cilastatin | 62.5 mg | 1 g | |
|  | 6.25 mg/kg | 25 mg/kg | |
| Meropenem | | | 40 mg/kg |
|  | 0.5 mg/kg | 2.5 mg/kg | |
| 2$^{ND}$ GEN CEPHS | | | |
| Cefaclor | 62.5 mg | 500 mg | |
|  | 5 mg/kg/day | 40 mg/kg/day | |
| Cefotetan | 0.125 g | 3 g | |
|  | 10 mg/kg/day | 80 mg/kg/day | |
| Cefoxitin | 0.25 g | 3 g | |
|  | 20 mg/kg/day | 160 mg/kg/day | |
| Cefprozil | 62.5 mg | 500 mg | |
|  | 1.875 mg/kg/dose | 15 mg/kg/dose | |
| Cefuroxime | 187.5 mg | 3 g | |
|  | 31.25 mg | 500 mg | |
|  | 12.5 mg/kg/day | 150 mg/kg/day | |
|  | 31.25 mg/kg/day | 500 mg/kg/day | |
| Loracarbef | 50 mg | 400 mg | |
|  | 3.75 mg/kg/day | 500 mg/kg/day | |
| 3$^{RD}$ GEN CEPHS | | | |
| Cefdinir | 75 mg | | 600 mg qd |
| Cefixime | 50 mg | | 400 mg |
| Cefoperazone | 0.25 g/day | 12 g/day | |
|  | 25 mg/kg/day | 150 mg/kg/day | |
| Cefotaxime | 0.25 g | 2 g | |
|  | 12.5 mg/kg/dose | 300 mg/kg/day | |
| Cefpodoxime | 25 mg | 400 mg | 10 mg/kg/day |
| Ceftazidime | 62.5 mg | 2 g q8 | |
|  | 25 mg/kg/day | 150 mg/kg/day | |
| Ceftibuten | 2.25 mg/kg | 400 mg | 400 mg |
| Ceftozoxime | 0.25 g | 4 g | |
|  | 12.5 mg/kg/day | 200 mg/kg/day | |
| Ceftriaxone | 31.25 mg | 2 g | |
|  | 12.5 mg/kg/day | 100 mg/kg/day | |
| 4$^{TH}$ GEN CEPHS | | | |
| Cefepime | 0.125 g | 2 g | |
|  | 12.5 mg/kg | 50 mg/kg q8 | |
| MACROLIDES | | | |
| Azithromycin | 62.5 mg | 500 mg | |
|  | 62.5 mg | 500 mg | |
| Clarithromycin | 62.5 mg | 500 mg | 7.5 mg/kg/day |
| Dirithromycin | | | 500 mg |
| 3$^{RD}$ GEN PENS | | | |
| Amoxicillin | 62.5 mg | 875 mg | |
|  | 5 mg/kg/day | 45 mg/kg | |

TABLE 3-continued

Gram-Negative Antibiotics That May Be Used
In a Combination Therapy with The Compound of Formula I

| AGENTS | LO DOSE | HI DOSE | STD DOSE |
|---|---|---|---|
| Amoxicillin/clavulanic acid | 62.5 mg | 875 mg | |
|  | 6.25 mg/kg/day | 45 mg/kg/day | |
| Ampicillin | 62.5 mg | 12 g/day q4 | |
|  | 6.25 mg/kg/day | 300 mg/kg/day | |
| Ampicillin/sulbactam | 0.375 g | 3 g | 300 mg/kg/day |
| 4$^{TH}$ GEN PENS | | | |
| Mezlocillin | 0.375 g | 4 g | 75 mg/kg |
| Piperacillin | 1.5 g/day | 24 g day | |
|  | 25 mg/kg/day | 300 mg/kg/day | |
| Piperacillin/tazobactam | | | 240 mg/kg/day |
| Ticarcillin | 0.25 g | 4 g | |
|  | 12.5 mg/kg/day | 300 mg/kg/day | |
| Ticarcillin/clavulanate | 50 mg/kg/day | 300 mg/kg/day | |
|  | 0.775 g | 3.1 g | |
| 1$^{ST}$ GEN QUINOLONES | | | |
| Nalidixic Acid | | | 55 mg/kg/day |
| 2$^{ND}$ GEN QUINOLONES | | | |
| Ciprofloxacin | 50 mg | 750 mg | |
|  | 2.5 mg/kg/dose | 15 mg/kg/dose | |
|  | 62.5 mg | 750 mg | |
|  | 2.5 mg/kg/dose | 15 mg/kg/dose | |
| Enoxacin | 50 mg | 400 mg | |
| Lomefloxacin | | | 400 mg |
| Norfloxacin | | | 400 mg |
| Ofloxacin | 50 mg | 400 mg | |
| 3$^{RD}$ GEN QUINOLONES | | | |
| Levofloxacin | 62.5 mg | 750 mg | |
| Sparfloxacin | 50 mg | 400 mg | |
| 4$^{TH}$ GEN QUINOLONES | | | |
| Alatrofloxacin | 50 mg | 300 mg | |
| Gatifloxacin | 50 mg | 400 mg | |
| Moxifloxacin | | | 400 mg |
| SULFAS | | | |
| Trimethoprim/sulfamehoxazole | 15/200 mg | | |
|  | 3.75 mg/day | 150 mg/day | |
| Sulfisoxazole | 18.75 mg | 150 mg | |
| Sulfamethoxazole | 0.25 g | 2 g | |
| TETRACYCLINES | | | |
| Doxycycline | 5 mg | 100 mg | |
| Minocycline | 25 mg | 200 mg | |
| Tetracycline | 62.5 mg | 500 mg | |
| OTHER | | | |
| Chloramphenicol | 12.5 mg/kg/day | 100 mg/kg/day | |
| Aztreonam | 125 mg | 2 g | |
|  | 37.5 mg | 450 mg | |
|  | 5 mg/kg/day | 40 mg/kg/day | |
|  | 2 mg/kg/day | 25 mg/kg/day | |
| Fosfomycin | | | 3 g |
| Nitrofurantoin | 12.5 mg | 100 mg | |
|  | 1.25 mg/kg/day | 7 mg/kg/day | |
|  | 2.5 mg/kg | 600 mg/kg | |
| Trimethoprim | 25 mg | 200 mg | 10 mg/kg/day |

In Tables 2 and 3, the term "Lo Dose" means the recommended lower dosage for the combination therapy of the invention. It may be adjusted even lower depending on the requirements of each subject being treated and the severity of the bacterial infection. The lowest dosage possible may be 0.1 mg when combined with the compound of formula I of the present invention. The term "Hi Dose" means the recommended highest dosage in the combination therapy. It may be changed hereafter according to the US FDA standard. The term "Std Dose" means the recommended standard dosage for the combination therapy of the present invention. It may be adjusted even lower depending on the requirements of each subject being treated and the severity of the bacterial infection. A specific antibiotic may have more than one the recommended dosage ranges.

Generally, an antibacterially effective amount of dosage of the compound of formula I of the present invention, either administered individually or in combination with other antibiotics, will be in the range of about 0.1 to about 400, more preferably about 1.0 to about 50 mg/kg of body weight/day. It is to be understood that the dosages of active component(s) may vary depending upon the requirements of each subject being treated and the severity of the bacterial infection.

The desired dose may conveniently be presented in a single dose or as divided into multiple doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Also, it is to be understood that the initial dosage administered may be increased beyond the above upper level in order to rapidly achieve the desired plasma concentration. On the other hand, the initial dosage may be smaller than the optimum and the daily dosage may be progressively increased during the course of treatment depending on the particular situation.

For the combination therapy, the compound of formula I may be administered concurrently or concomitantly with other antibiotics. The term "concurrently" means the subject being treated takes one drug within about 5 minutes of taking the other drug. The term "concomitantly" means the subject being treated takes one drug within the same treatment period of taking the other drug. The same treatment period is preferably within twelve hours and up to forty-eight hours.

For the combination therapy, the compound of formula I, and one or more other antibiotics may be administered in the same physical form or separately, i.e., they may be administered in the same delivery vehicle or in different delivery vehicles.

For the combination therapy, some of the antibiotics may further be used with a β-Lactamase inhibitor. For example, Imipenem may be used with cilastatin, Ampicillin may be used with sulbactam, Piperacillin may be used with tazobactam, and Ampicillin may be used with sulbactam.

Specifically, the combination therapy of the present invention is the compound of formula I of the present invention with Amikacin.

Specifically, the combination therapy of the present invention is the compound of formula I of the present invention with Gentamicin.

Specifically, the combination therapy of the present invention is the compound of formula I of the present invention with Spectinomycin.

Specifically, the combination therapy of the present invention is the compound of formula I of the present invention with Tobramycin.

Specifically, the combination therapy of the present invention is the compound of formula I of the present invention with Imipenem/cilastatin.

Specifically, the combination therapy of the present invention is the compound of formula I of the present invention with Meropenem.

Specifically, the combination therapy of the present invention is the compound of formula I of the present invention with Cefadroxil.

Specifically, the combination therapy of the present invention is the compound of formula I of the present invention with Cefazolin.

Specifically, the combination therapy of the present invention is the compound of formula I of the present invention with Cephalexin.

Specifically, the combination therapy of the present invention is the compound of formula I of the present invention with Cefaclor.

Specifically, the combination therapy of the present invention is the compound of formula I of the present invention with Cefotetan.

Specifically, the combination therapy of the present invention is the compound of formula I of the present invention with Cefoxitin.

Specifically, the combination therapy of the present invention is the compound of formula I of the present invention with Cefprozil.

Specifically, the combination therapy of the present invention is the compound of formula I of the present invention with Cefuroxime.

Specifically, the combination therapy of the present invention is the compound of formula I of the present invention with Loracarbef.

Specifically, the combination therapy of the present invention is the compound of formula I of the present invention with Cefdinir.

Specifically, the combination therapy of the present invention is the compound of formula I of the present invention with Cefixime.

Specifically, the combination therapy of the present invention is the compound of formula I of the present invention with Cefoperazone.

Specifically, the combination therapy of the present invention is the compound of formula I of the present invention with Cefotaxime.

Specifically, the combination therapy of the present invention is the compound of formula I of the present invention with Cefpodoxime.

Specifically, the combination therapy of the present invention is the compound of formula I of the present invention with Ceftazidime.

Specifically, the combination therapy of the present invention is the compound of formula I of the present invention with Ceftibuten.

Specifically, the combination therapy of the present invention is the compound of formula I of the present invention with Ceftozoxime.

Specifically, the combination therapy of the present invention is the compound of formula I of the present invention with Ceftriaxone.

Specifically, the combination therapy of the present invention is the compound of formula I of the present invention with Cefepime.

Specifically, the combination therapy of the present invention is the compound of formula I of the present invention with Azithromycin.

Specifically, the combination therapy of the present invention is the compound of formula I of the present invention with Clarithromycin.

Specifically, the combination therapy of the present invention is the compound of formula I of the present invention with Dirithromycin.

Specifically, the combination therapy of the present invention is the compound of formula I of the present invention with Penicillin G.

Specifically, the combination therapy of the present invention is the compound of formula I of the present invention with Cloxacillin.

Specifically, the combination therapy of the present invention is the compound of formula I of the present invention with Dicloxacillin.

Specifically, the combination therapy of the present invention is the compound of formula I of the present invention with Nafcillin.

Specifically, the combination therapy of the present invention is the compound of formula I of the present invention with Oxacillin.

Specifically, the combination therapy of the present invention is the compound of formula I of the present invention with Amoxicillin.

Specifically, the combination therapy of the present invention is the compound of formula I of the present invention with Amoxicillin/clavulanic acid.

Specifically, the combination therapy of the present invention is the compound of formula I of the present invention with Ampicillin.

Specifically, the combination therapy of the present invention is the compound of formula I of the present invention with Ampicillin/sulbactam.

Specifically, the combination therapy of the present invention is the compound of formula I of the present invention with Mezlocillin.

Specifically, the combination therapy of the present invention is the compound of formula I of the present invention with Piperacillin.

Specifically, the combination therapy of the present invention is the compound of formula I of the present invention with Piperacillin/tazobactam.

Specifically, the combination therapy of the present invention is the compound of formula I of the present invention with Ticarcillin.

Specifically, the combination therapy of the present invention is the compound of formula I of the present invention with Ticarcillin/clavulanate.

Specifically, the combination therapy of the present invention is the compound of formula I of the present invention with Nalidixic Acid.

Specifically, the combination therapy of the present invention is the compound of formula I of the present invention with Ciprofloxacin.

Specifically, the combination therapy of the present invention is the compound of formula I of the present invention with Enoxacin.

Specifically, the combination therapy of the present invention is the compound of formula I of the present invention with Lomefloxacin.

Specifically, the combination therapy of the present invention is the compound of formula I of the present invention with Norfloxacin.

Specifically, the combination therapy of the present invention is the compound of formula I of the present invention with Ofloxacin.

Specifically, the combination therapy of the present invention is the compound of formula I of the present invention with Levofloxacin.

Specifically, the combination therapy of the present invention is the compound of formula I of the present invention with Sparfloxacin.

Specifically, the combination therapy of the present invention is the compound of formula I of the present invention with Alatrofloxacin.

Specifically, the combination therapy of the present invention is the compound of formula I of the present invention with Gatifloxacin.

Specifically, the combination therapy of the present invention is the compound of formula I of the present invention with Moxifloxacin.

Specifically, the combination therapy of the present invention is the compound of formula I of the present invention with Trimethoprim/sulfamethoxazole.

Specifically, the combination therapy of the present invention is the compound of formula I of the present invention with Sulfisoxazole.

Specifically, the combination therapy of the present invention is the compound of formula I of the present invention with Sulfamethoxazole.

Specifically, the combination therapy of the present invention is the compound of formula I of the present invention with Doxycycline.

Specifically, the combination therapy of the present invention is the compound of formula I of the present invention with Minocycline.

Specifically, the combination therapy of the present invention is the compound of formula I of the present invention with Tetracycline.

Specifically, the combination therapy of the present invention is the compound of formula I of the present invention with Aztreonam.

Specifically, the combination therapy of the present invention is the compound of formula I of the present invention with Chloramphenicol.

Specifically, the combination therapy of the present invention is the compound of formula I of the present invention with Clindamycin.

Specifically, the combination therapy of the present invention is the compound of formula I of the present invention with Quinupristin/dalfopristin.

Specifically, the combination therapy of the present invention is the compound of formula I of the present invention with Fosfomycin.

Specifically, the combination therapy of the present invention is the compound of formula I of the present invention with Metronidazole.

Specifically, the combination therapy of the present invention is the compound of formula I of the present invention with Nitrofurantoin.

Specifically, the combination therapy of the present invention is the compound of formula I of the present invention with Rifampin.

Specifically, the combination therapy of the present invention is the compound of formula I of the present invention with Trimethoprim.

Specifically, the combination therapy of the present invention is the compound of formula I of the present invention with Vancomycin.

Routes of Administration

In therapeutic use for treating, or combating, bacterial infections in a mammal (i.e. human and animals) the compound of formula I, either individually, or in combination with other antibiotics can be administered orally, parenterally, topically, rectally, or intranasally.

Parenteral administrations include injections to generate a systemic effect or injections directly to the afflicted area. Examples of parenteral administrations are subcutaneous, intravenous, intramuscular, intradermal, intrathecal, intraocular, intravetricular, and general infusion techniques.

Topical administrations include the treatment of infectious areas or organs readily accessibly by local application, such as, for example, eyes, ears including external and middle ear infections, vaginal, open and sutured or closed wounds and skin. It also includes transdermal delivery to generate a systemic effect.

The rectal administration includes the form of suppositories.

The intranasally administration includes nasal aerosol or inhalation applications.

The preferred routes of administration are oral and intravenous.

Pharmaceutical compositions of the compound of formula I, either individually or in combination with other antibiotics, may be prepared by methods well known in the art, e.g., by means of conventional mixing, dissolving, granulation, dragee-making, levigating, emulsifying, encapsulating, entrapping, lyophilizing processes or spray drying.

Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, solutions, emulsions, gels, syrups, slurries, suspensions and the like, for oral ingestion by a patient. A carrier can be at least one substance which may also function as a diluent, flavoring agent, solubilizer, lubricant, suspending agent, binder, tablet disintegrating agent, and encapsulating agent. Examples of such carriers or excipients include, but are not limited to, magnesium carbonate, magnesium stearate, talc, sugar, lactose, sucrose, pectin, dextrin, mnnitol, sorbitol, starches, gelatin, cellulosic materials, low melting wax, cocoa butter or powder, polymers such as polyethylene glycols and other pharmaceutical acceptable materials.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identificatin or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, liquid polyethylene glycols, cremophor, capmul, medium or long chain mono-, fi- or triglycerides. Stabilizers may be added in these formulations, also.

Liquid form compositions include solutions, suspensions and emulsions. For example, there may be provided solutions of the compounds of this invention dissolved in water and water-propylene glycol and water-polyethylene glycol systems, optionally containing suitable conventional coloring agents, flavoring agents, stabilizers and thickening agents.

The compounds may also be formulated for parenteral administration, e.g., by injections, bolus injection or continuous infusion. Formulations for parenteral administration may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

For injection, the compounds of the invention may be formulated in aqueous solution, preferably in physiologically compatible buffers or physiological saline buffer. Suitable buffering agents include trisodium orthophosphate, sodium bicarbonate, sodium citrate, N-methylglucamine, L(+)-lysine and L(+)-arginine.

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Other parenteral administrations also include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in a powder form for constitution with a suitable vehicle, e.g., sterile, pyrogen-free water, before use.

For suppository administration, the compounds may also be formulated by mixing the agent with a suitable non-irritating excipient which is solid at room temperature but liquid at rectal temperature and therefore will melt in the rectum to release the drug. Such materials include cocoa butter, beeswax and other glycerides.

For administration by inhalation, compounds of the present invention can be conveniently delivered through an aerosol spray in the form of solution, dry powder, or cream. The aerosol may use a pressurized pack or a nebulizer and a suitable propellant. In the case of a pressurized aerosol, the dosage unit may be controlled by providing a valve to deliver a metered amount. Capsules and cartridges of, for example, gelatin for use in an inhaler may be formulated containing a power base such as lactose or starch.

For topical applications, the pharmaceutical composition may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Aternatively, the pharmaceutical compositions can be formulated in a suitable lotion such as suspensions, emulsion, or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic and otitis uses, the pharmaceutical compositions may be formulated as micronized suspensions in isotonic, pH adjusted sterile saline, or preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

In addition to the formulations described previously, the compounds may also be formulated as depot preparations. Such long acting formulations may be in the form of implants. A compound of this invention may be formulated for this route of administration with suitable polymers, hydrophbic materials, or as a sparing soluble derivative such as, without limitation, a sparingly soluble salt.

Additionally, the compounds may be delivered using a sustained-release system. Various sustained-release materials have been established and are well known by those skilled in the art. Sustained-release capsules may, depending on their chemical nature, release the compounds for 24 hours up to several days. Depending on the chemical nature and the biological stability of the therapeutic reagent, additional strategies for protein stabilization may be employed.

The compound of formula I, or its combination therapy may be administered intravenously in a form of aqueous solution. The suitable antibiotics for this IV aqueous solution are: Amikacin, Azetreonam, Gentamicin, Tobramycin, Imipenem, Meropenem, Cefotetan, Cefoxitin, Cefuroxime, Cefoperazone, Cefotaxime, Ceftazidime, Ceftozoxime, Ceftriaxone, Cefepime, Azithromycin, Ampicillin, Mezlocillin, Piperacillin, Ticarcillin, Ciprofloxacin, Levofloxacin, Alatrofloxacin, Gatifloxacin, Minocycline, Chloramphenicol, Clindamycin, Metronidazole, Vancomycin, Cefazolin, Penicillin G, Nafcillin, Ofloxacin and Oxaxillin.

The preferred IV solution for the compound of formula I is:

| | |
|---|---|
| The compound of formula I | 2.0 mg/mL |
| Sodium Citrate Dihydrate (USP) | 1.64 mg/mL |
| Citric Acid Anhydrous (USP) | 0.85 mg/mL |
| Dextrose Monohydrate (USP) | 50.24 mg/mL |
| Hydrochloric Acid (10%) | q.s. to pH 4.8 (pH 4.6 to 5.0) |
| Sodium hydroxide (10%) | q.s. to pH 4.8 (pH 4.6 to 5.0) |
| Water for Injection (USP) | q.s.ad 1.0 mL |

The IV solution for the compound of formula I is formulated by heating water for injection to 60°. Next the sodium citrate, citric acid and dextrose are added and stirred until dissolved. An aqueous slurry of compound of formula I is added to the previous mixture and stirred until dissolved. The mixture is cooled to 25° with stirring. The pH is measured and adjusted if necessary. Last the mixture is brought to volume, if necessary, with water for injection. The mixture is filtered, filled into infusion containers, over wrapped and terminally moist heat sterilized.

The aqueous solution for IV administration can be placed in the container which is selected from the group consisting of a bag, a bottle, a vial, a large volume parenteral, a small volume parenteral, a prefilled syringe and a cassette. It is realized that a vial is a bottle. However, those skilled in the art use the term "bottle" to refers to larger bottles and "vials" to refer to smaller bottles. It is preferred that the container be a bag, a bottle, a vial or a prefilled syringe. It is more preferred that the container be a bag or bottle. It is most preferred that the container be a bag. The shape and/or size of the container is unimportant. It is preferred that the container be a bag sufficient to hold 25 to 2,000 mL of IV solution. It is preferred that the compound of formula I mixture be put in bags in amounts of 100, 200 or 300 mL of solution however smaller or larger volumes are acceptable.

It is well known to those skilled in the art that an IV solution must be sterile. While there are a number of methods to sterilize an IV solution, it is preferred to terminally moist heat or steam sterilize IV solutions of the compound of formula I. When the term terminally "moist heat sterilize" is used, it refers to and includes steam sterilization.

When terminally moist heat sterilizing an IV solution, the solution is placed in the container in which (1) it will be stored and then transferred to the container from which it will ultimately be administered, or (2) stored and then ultimately administered from the same container to deliver the IV solution to the patient. Therefore, it is imperative that the compound of formula I does not react with the container in which it is to be terminally moist heat sterilized and stored/stored-administered.

It has been found that when the container-solution contact surface is made of at least 50% polyolefin there is significantly much less loss of the compound of formula I during and following terminal moist heat sterilization. What is essential is that the container-solution contact surface material be primarily a polyolefin; the remainder of the container can be made from polyolefin or other materials. It is preferred that the container-solution contact surface is made of from about 50 to about 100% polyolefin. It is more preferred that the container-solution contact surface is made of from about 70 to about 90% polyolefin. It is more preferred that the container-solution contact surface is made of from about 80% polyolefin. It is even more preferred that the container-solution contact surface is made of polyolefin.

Polyolefins include, for example, polyethylene, polypropylene, polybutenes, polyisoprenes and polypentenes and copolymers and mixtures thereof. It is preferred that the polyolefin be selected from the group consisting of polyethylene and polypropylene. It is more preferred that the polyolefin be polypropylene or mixture of polypropylene and polyethylene.

The exact dosage and frequency of administration of the aqueous pharmaceutical composition depends on the particular combination of compound of formula I and antibacterial agent used, the particular condition being treated, the severity of the condition being treated, the age, weight, general physical condition of the particular patient, other medication the individual may be taking as is well known to those skilled in the art and can be more accurately determined by measuring the blood level or concentration of the antibacterial agents in the patient's blood and/or the patient's response to the particular condition being treated.

Definitions

All temperatures are in degrees Centigrade.

Physiological saline refers to an aqueous 0.9% sodium chloride solution.

When solvent pairs are used, the ratios of solvents used are volume/volume (v/v).

When the solubility of a solid in a solvent is used the ratio of the solid to the solvent is weight/volume (wt/v).

qsad refers to addition of a sufficient quantity of that material to bring the final composition to the specified volume.

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Preparation 1

The compound of formula I sterile solution:

| | |
|---|---|
| The compound of formula I | 2.0 mg/mL |
| Sodium Citrate Dihydrate (USP) | 1.64 mg/mL |
| Citric Acid Anhydrous (USP) | 0.85 mg/mL |
| Dextrose Monohydrate (USP) | 50.24 mg/mL |
| Hydrochloric Acid (10%) | q.s. to pH 4.8 (pH 4.6 to 5.0) |
| Sodium hydroxide (10%) | q.s. to pH 4.8 (pH 4.6 to 5.0) |
| Water for Injection (USP) | q.s.ad 1.0 mL |

Example 1

The Compound of Formula I and Gentamicin Sulfate

The compound of formula I sterile solution (PREPARATION 1) is admixed with commercial Gentamicin concentrate. One admixture is stored at 4° and another at 23°. The admixtures were sampled at one, three, five days and seven days. The samples were tested for both chemical and physical stability. The results of the samples for both temperatures show there is good chemical and physical stability over 7 days at 4° and 5 days at 23°. It is concluded that the admixture of compound of formula I and commercial Gentamicin concentrate is acceptable for human use.

Example 2

The Compound of Formula I and Tobramycin Sulfate

Following the general procedure of Example 1 and making non-critical variations, compound of formula I sterile solution (Preparation 1) is admixed with commercial Tobramycin concentrate. The results of the samples for both temperatures show there is good chemical and physical stability over 7 days at 4° and 1 day at 23°. It is concluded that the admixture of compound of formula I and commercial Tobramycin concentrate is acceptable for human use.

Example 3

The Compound of Formula I and Aztreonam

Following the general procedure of Example 1 and making non-critical variations, compound of formula I sterile solution (Preparation 1) is admixed with with commercial reconstituted Aztreonam. The results of the samples for both temperatures show there is good chemical and physical stability over 7 days at 4° and 7 days at 23°. It is concluded that the admixture of compound of formula I and commercial reconstituted Aztreonam is acceptable for human use.

Example 4

The Compound of Formula I and Cefazolin Sodium

Following the general procedure of Example 1 and making non-critical variations, compound of formula I sterile solution (Preparation 1) is admixed with commercial reconstituted Cefazolin. The results of the samples for both temperatures show there is good chemical and physical stability over 7 days at 40° and 3 day at 23°. It is concluded that the admixture of compound of formula I and commercial Cefazolin concentrate is acceptable for human use.

Example 5

The Compound of Formula I and Ceftazidime

Following the general procedure of Example 1 and making non-critical variations, compound of formula I sterile solution (Preparation 1) is admixed with commercial reconstituted Ceftazidime. The results of the samples for both temperatures show there is good chemical and physical stability over 7 days at 4° and 1 day at 23°. It is concluded that the admixture of compound of formula I and commercial Ceftazidime concentrate is acceptable for human use.

Example 6

The Compound of Formula I and Piperacillin Sodium

Following the general procedure of Example 1 and making non-critical variations, compound of formula I sterile solution (Preparation 1) is admixed with commercial reconstituted Piperacillin. The results of the samples for both temperatures show there is good chemical and physical stability over 7 days at 4° and 3 days at 23°. It is concluded that the admixture of compound of formula I and commercial Piperacillin concentrate is acceptable for human use.

Example 7

The Compound of Formula I and Ciprofloxacin

Following the general procedure of Example 1 and making non-critical variations, compound of formula I sterile solution (Preparation 1) is admixed with commercial ciprofloxacin concentrate. The results of the samples show there is good chemical and physical stability over 7 days at 23°. It is concluded that the admixture of compound of formula I and commercial ciprofloxacin concentrate is acceptable for human use.

Example 8

The Compound of Formula I and Ofloxacin

Following the general procedure of Example 1 and making non-critical variations, compound of formula I sterile solution (Preparation 1) is admixed with commercial Ofloxacin concentrate. The results of the samples for both temperatures show there is good chemical and physical stability over 7 days at 4° and 7 days at 23°. It is concluded that the admixture of compound of formula I and commercial Ofloxacin concentrate is acceptable for human use.

Example 9

The Compound of Formula I and Levofloxacin

Following the general procedure of Example 1 and making non-critical variations, compound of formula I sterile solution (Preparation 1) is admixed with commercial Levofloxacin concentrate. The results of the samples for both temperatures show there is good chemical and physical stability over 7 days at 4° and 7 days at 23°. It is concluded that the admixture of compound of formula I and commercial Levofloxacin concentrate is acceptable for human use.

We claim:

1. A compound of formula I

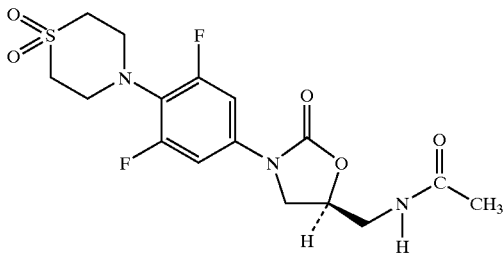

or a pharmaceutically acceptable salt thereof.

2. N-({(5S)-3-[4-(1,1-dioxido-4-thiomorpholinyl)-3,5-difluorophenyl]-2-oxo-1,3-oxazolidin-5-yl}methyl) acetamide of claim 1.

3. A method for treating bacteria infections comprising administering to a mammal being treated a pharmaceutically effective amount of the compound of claim 1.

4. The method of claim 3, wherein the compound of claim 1 is administered parenterally, topically, rectally or intranasally.

5. The method of claim 3, wherein the compound of claim 1 is administered orally.

6. The method of claim 4 wherein parenteral administration is subcutaneous, intravenous, intramuscular, intradermal, intrathecal, intraocular, intravetricular injection.

7. The method of claim 3 wherein said compound is administered in an amount of from about 0.1 to about 100 mg/kg of body weight/day.

8. The method of claim 3 wherein said compound is administered in an amount of from about 1 to about 50 mg/kg of body weight/day.

9. The method of claim 3 wherein said infection is skin infection.

10. The method of claim 3 wherein the infection is eye infection.

11. The method of claim 3 wherein said mammal is human.

12. The method of claim 3 wherein said mammal is an animal.

13. A pharmaceutical composition comprising the compound of claim 1 or its pharmaceutically acceptable salts thereof and a pharmaceutically acceptable carrier.

14. An aqueous pharmaceutical composition for IV administration of the compound of claim 1 or its pharmaceutically acceptable salts thereof and pharmaceutically acceptable carrier.

15. An aqueous pharmaceutical composition according to claim 14 where the aqueous composition is a solution.

16. An aqueous pharmaceutical composition according to claim 15 where the solution is sterile.

17. An aqueous pharmaceutical composition according to claim 14 where the IV pharmaceutical composition is in a container where the container-solution contact surface material made of at least 50% polyolefin.

18. An aqueous pharmaceutical composition according to claim 17 where the container is a bag, a bottle, a vial, a large volume parenteral, a small volume parenteral, a prefilled syringe, or a cassette.

19. An aqueous pharmaceutical composition according to claim 18 where the container is a bag, a bottle, a vial, or a prefilled syringe.

20. An aqueous pharmaceutical composition according to claim 17 where the container-solution contact surface is made of polyolefin or made primarily of polyolefin.

21. An aqueous pharmaceutical composition according to claim 20 where the container-solution contact surface is made of from about 50 to about 100% polyolefin.

22. An aqueous pharmaceutical composition according to claim 20 where the container-solution contact surface is made of from about 70 to about 90% polyolefin.

23. An aqueous pharmaceutical composition according to claim 20 where the container-solution contact surface is made of polyolefin.

24. An aqueous pharmaceutical composition according to claim 23 where the polyolefin is selected from the group consisting of polyethylene, polypropylene, polybutenes, polyisoprenes and polypentenes and copolymers and mixtures thereof.

25. A composition comprising:
    (a) a pharmaceutically effective amount of the compound of formula I as shown in claim 1 or a pharmaceutically effective salt thereof; (b) a pharmaceutically effective amount of one or more antibiotics or a pharmaceutically effective salt thereof; and (c) a pharmaceutically acceptable carrier.

26. The composition of claim 25 wherein the antibiotic is Amikacin, Gentamicin, Spectinomycin, Tobramycin, Imipenem, Meropenem, Cefadroxil, Cefazolin, Cephalexin, Cefaclor, Cefotetan, Cefoxitin, Cefprozil, Cefuroxime, Loracarbef, Cefdinir, Cefixime, Cefoperazone, Cefotaxime, Cefpodoxime, Ceftazidime, Ceftibuten, Ceftozoxime, Ceftriaxone, Cefepime, Azithromycin, Clarithromycin, Dirithromycin, Penicillin G, Cloxacillin, Dicloxacillin, Nafcillin, Oxacillin, Amoxicillin, Ampicillin, Mezlocillin, Piperacillin, Nalidixic Acid, Ciprofloxacin, Enoxacin, Lomefloxacin, Norfloxacin, Ofloxacin, Levofloxacin, Sparfloxacin, Alatrofloxacin, Gatifloxacin, Moxifloxacin, Trimethoprim, Sulfisoxazole, Sulfamethoxazole, Doxycycline, Minocycline, Tetracycline, Aztreonam, Chloramphenicol, Clindamycin, Quinupristin, Fosfomycin, Metronidazole, Nitrofurantoin, Rifampin, Trimethoprim, and Vancomycin.

27. An aqueous pharmaceutical composition for IV administration comprising: (a) pharmaceutically effective amount of the compound of claim 1 or a pharmaceutically effective salt thereof; and (b)) a pharmaceutically effective amount of at least one antibiotic selected from the group consisting of Amikacin, Azetreonam, Gentamicin, Tobramycin, Imipenem, Meropenem, Cefotetan, Cefoxitin, Cefuroxime, Cefoperazone, Cefotaxime, Ceftazidime, Ceftozoxime, Ceftriaxone, Cefepime, Azithromycin, Ampicillin, Mezlocillin, Piperacillin, Ticarcillin, Ciprofloxacin, Levofloxacin, Alatrofloxacin, Gatifloxacin, Minocycline, Chloramphenicol, Clindamycin, Metronidazole, Vancomycin, Cefazolin, Penicillin G, Nafcillin, Ofloxacin and Oxaxillin.

28. An aqueous pharmaceutical composition according to claim 27 where the aqueous composition is a solution.

29. An aqueous pharmaceutical composition according to claim 27 where the solution is sterile.

30. An aqueous pharmaceutical composition according to claim 27 wherein the IV pharmaceutical composition is in a container where the container-solution contact surface material made of at least 50% polyolefin.

31. An aqueous pharmaceutical composition according to claim 30 wherein the container is a bag, a bottle, a vial, a large volume parenteral, a small volume parenteral, a prefilled syringe or a cassette.

32. An aqueous pharmaceutical composition according to claim 31 where the container is a bag, a bottle, a vial or a prefilled syringe.

33. An aqueous pharmaceutical composition according to claim 30 where the container-solution contact surface is made of polyolefin or made primarily of polyolefin.

34. An aqueous pharmaceutical composition according to claim 30 wherein the container-solution contact surface is made of from about 50 to about 100% polyolefin.

35. An aqueous pharmaceutical composition according to claim 30 wherein the container-solution contact surface is made of from about 70 to about 90% polyolefin.

36. An aqueous pharmaceutical composition according to claim 30 wherein the container-solution contact surface is made of polyolefin.

37. An aqueous pharmaceutical composition according to claim 36 wherein the polyolefin is polyethylene, polypropylene, polybutenes, polyisoprenes, polypentenes or copolymers and mixtures thereof.

38. A method for treating bacteria infections in a mammal comprising administering to said mammal (a) a pharmaceutically effective amount of the compound of claim 1 or a pharmaceutically effective salt thereof; and (b) a pharmaceutically effective amount of at least one antibiotic or a pharmaceutically effective salt thereof.

39. The method of claim 38 wherein the antibiotic is Amikacin, Gentamicin, Spectinomycin, Tobramycin, Imipenem, Meropenem, Cefadroxil, Cefazolin, Cephalexin, Cefaclor, Cefotetan, Cefoxitin, Cefprozil, Cefuroxime, Loracarbef, Cefdinir, Cefixime, Cefoperazone, Cefotaxime, Cefpodoxime, Ceftazidime, Ceftibuten, Ceftozoxime, Ceftriaxone, Cefepime, Azithromycin, Clarithromycin, Dirithromycin, Penicillin G, Cloxacillin, Dicloxacillin, Nafcillin, Oxacillin, Amoxicillin, Ampicillin, Mezlocillin, Piperacillin, Nalidixic Acid, Ciprofloxacin, Enoxacin, Lomefloxacin, Norfloxacin, Ofloxacin, Levofloxacin, Sparfloxacin, Alatrofloxacin, Gatifloxacin, Moxifloxacin, Trimethoprim, Sulfisoxazole, Sulfamethoxazole, Doxycycline, Minocycline, Tetracycline, Aztreonam, Chloramphenicol, Clindamycin, Quinupristin, Fosfomycin, Metronidazole, Nitrofurantoin, Rifampin, Trimethoprim, or Vancomycin.

40. A method for treating bacteria infections caused by gram-positive bacteria in a mammal comprising administering to said mammal (a) a pharmaceutically effective amount of compound of the formula I as shown in claim 1 or a pharmaceutically effective salt thereof; and (b) a pharmaceutically effective amount of at least one antibiotic or a pharmaceutically effective salt thereof.

41. The method of claim 40 wherein the antibiotic is Amikacin, Gentamicin, Spectinomycin, Tobramycin, Imipenem, Meropenem, Cefadroxil, Cefazolin, Cephalexin, Cefaclor, Cefotetan, Cefoxitin, Cefprozil, Cefuroxime, Loracarbef, Cefdinir, Cefixime, Cefoperazone, Cefotaxime, Cefpodoxime, Ceftazidime, Ceftibuten, Ceftozoxime, Ceftriaxone, Cefepime, Azithromycin, Clarithromycin, Dirithromycin, Penicillin G, Cloxacillin, Dicloxacillin, Nafcillin, Oxacillin, Amoxicillin, Ampicillin, Mezlocillin, Piperacillin, Nalidixic Acid, Ciprofloxacin, Enoxacin, Lomefloxacin, Norfloxacin, Ofloxacin, Levofloxacin, Sparfloxacin, Alatrofloxacin, Gatifloxacin, Moxifloxacin, Trimethoprim, Sulfisoxazole, Sulfamethoxazole, Doxycycline, Minocycline, Tetracycline, Chloramphenicol, Clindamycin, Quinupristin/dalfopristin, Fosfomycin, Nitrofurantoin, Rifampin, Trimethoprim, or Vancomycin.

42. A method for treating bacteria infections caused by gram-negative bacteria in a mammal comprising administering to said mammal (a) a pharmaceutically effective amount of the compound of claim 1 or a pharmaceutically effective salt thereof; and (b) a pharmaceutically effective amount of one or more antibiotics or a pharmaceutically effective salt thereof.

43. The method of claim 42 wherein the antibiotic is Amikacin, Gentamicin, Spectinomycin, Tobramycin, Imipenem, Meropenem, Cefaclor, Cefotetan, Cefoxitin, Cefprozil, Cefuroxime, Loracarbef, Cefdinir, Cefixime, Cefoperazone, Cefotaxime, Cefpodoxime, Ceftazidime, Ceftibuten, Ceftozoxime, Ceftriaxone, Cefepime, Azithromycin, Clarithromycin, Dirithromycin, Amoxicillin, Amoxicillin, Ampicillin, Ampicillin, Mezlocillin, Piperacillin, Piperacillin, Nalidixic Acid, Ciprofloxacin, Enoxacin, Lomefloxacin, Norfloxacin, Ofloxacin, Levofloxacin, Sparfloxacin, Alatrofloxacin, Gatifloxacin, Moxifloxacin, Trimethoprim, Sulfisoxazole, Sulfamethoxazole, Doxycycline, Minocycline, Tetracycline, Aztreonam, Chloramphenicol, Fosfomycin, Nitrofurantoin, or Trimethoprim.

44. The method of claims 35–43 wherein the compound of formula I and the other antibiotic are administered parenterally, topically, rectally, or intranasally.

45. The method of claims 35–43 wherein the compound of formula I and the other antibiotic are administered orally.

46. The method of claim 44 wherein parenteral administration is subcutaneous, intravenous, intramuscular, intradermal, intrathecal, intraocular, intravetricular injection.

47. The method of claims 35–43 wherein said infection is skin infection.

48. The method of claims 35–43 wherein said mammal is human.

49. The method of claims 35–43 wherein said mammal is an animal.

50. The method of claims 44 wherein the compound of formula I and the antibiotic are concomitantly administered.

51. The method of claims 44 wherein the compound of formula I and the antibiotics are concurrently administered.

* * * * *